United States Patent [19]
Packard

[11] Patent Number: 4,475,619
[45] Date of Patent: Oct. 9, 1984

[54] STETHOSCOPE WITH FLOATING DIAPHRAGM

[75] Inventor: Thomas J. Packard, St. Paul, Minn.

[73] Assignee: Minnesota Mining and Manufacturing Company, St. Paul, Minn.

[21] Appl. No.: 478,222

[22] Filed: Mar. 24, 1983

[51] Int. Cl.³ .......................... A61B 7/02; H04R 25/00
[52] U.S. Cl. ................................................. 181/137
[58] Field of Search .............. 181/131, 137, 157, 158, 181/132

[56] References Cited

U.S. PATENT DOCUMENTS

| | | | |
|---|---|---|---|
| 2,356,262 | 8/1944 | Mott | 181/137 X |
| 3,108,652 | 10/1963 | Littmann | 181/131 |
| 3,109,508 | 11/1963 | Cefaly | 181/137 |
| 3,152,659 | 10/1964 | Littmann | 181/137 |
| 3,157,246 | 11/1964 | Howell | 181/137 |
| 3,179,204 | 4/1965 | Cefaly | 181/137 |
| 3,215,224 | 11/1965 | Machlup | 181/137 |
| 3,224,526 | 12/1965 | Weber | 181/137 |
| 3,276,536 | 10/1966 | Littmann | 181/137 |
| 3,303,903 | 2/1967 | Speelman | 181/131 |
| 3,307,650 | 3/1967 | Howell | 181/137 |
| 3,515,239 | 6/1970 | Machlup et al. | 181/137 |
| 3,587,776 | 6/1971 | Haiken | 181/137 |
| 4,440,258 | 4/1984 | Packard | 181/137 |

OTHER PUBLICATIONS

Dawson, J. B., B.M., M.R.C.P.Ed., "Auscultation and the Stethoscope", *The Practioner*, vol. 193, pp. 315-322, Sep. 1964.

Primary Examiner—Benjamin R. Fuller
Attorney, Agent, or Firm—Donald M. Sell; James A. Smith; Robert W. Hoke, II

[57] ABSTRACT

A stethoscope including a diaphragm head with a loosely affixed diaphragm exhibiting an increased frequency response range. The diaphragm is peripherally supported adjacent the rim of the diaphragm head. The diaphragm is contacted with the head by the pressure applied by the underlying skin or clothing of the patient to eliminate sound leakage therebetween.

11 Claims, 3 Drawing Figures

STETHOSCOPE WITH FLOATING DIAPHRAGM

BACKGROUND OF THE INVENTION

The present invention relates to stethoscopes. More particularly, it relates to the head or chest piece portion of a stethoscope and to improved means for mounting a diaphragm on the chest piece.

Stethoscope chest pieces or heads are typically constructed with opposed bell and diaphragm sides or heads. Stethoscope heads of this type are described in U.S. Pat. Nos. 3,108,652; 3,152,659; 3,215,224; 3,224,526; 3,276,536; 3,303,903; and 3,515,239.

The diaphragm used in stethoscope heads has a relatively high degree of acoustical stiffness. Acoustical stiffness is a function of the mechanical stiffness of the diaphragm, the thickness and diameter of the diaphragm and the manner in which the diaphragm is suspended or supported within the stethoscope head. The higher the degree of acoustical stiffness, the greater the attenuation of low frequency sounds. Hence, the diaphragm side of the stethoscope head is primarily used to monitor high frequency sounds.

The open bell side of the stethoscope head, on the other hand, is generally used to monitor low frequency sounds. Although the bell captures all of the sound energy within its periphery, it is best suited for monitoring low frequency sounds. This is primarily a consequence of the psychoacoustic phenomenon whereby low frequency sounds tend to mask high frequency sounds. For example, if there are sounds of two different frequencies within the volume of the bell, the lower frequency sound will tend to dominate. Also, in the case of the human body, it is the lower frequency sounds that generally have the greater energy. This heightens the masking of the higher frequency sounds by the lower frequency sounds.

One major drawback of stethoscope heads having opposed diaphragm and bell sides heads is that the wearer must remove the chest piece from the patient's skin in order to switch from one side to the other. This results in an interruption in the sound pattern between high and low frequency sounds and makes subtle abnormalities more difficult to detect.

Stethoscope head constructions are known which are designed to permit detection of a range of frequencies without the physician having to remove the stethoscope head from the patient's skin. For example, U.S. Pat. No. 3,109,508 discloses a stethoscope head which comprises three sound receiving heads. One of the sound receiving heads comprises a diaphragm which can be distorted to vary the volume of the chamber enclosed by the diaphragm. Concommitment with the change in volume of the chamber is a change in the acoustical stiffness of the diaphragm. The ability to change the volume of the chamber is said to permit "tuning in" of the particular sound or vibration to be detected. Unfortunately, the frequency response of this particular sound receiving head is not believed to be optimized. Even in its totally relaxed state where the acoustical stiffness is minimized and the sensitivity to low frequency sounds is maximized, the diaphragm still exhibits an acoustical stiffness which is not optimized for detection of low frequency sounds. This is a result of the traditional manner in which diaphragms have been tightly or rigidly affixed to the heads. Consequently, it is often necessary to employ one of the other two sound receiving heads in the detection of sounds of such frequency.

U.S. Pat. No. 3,157,246 discloses a stethoscope construction comprising a diaphragm which is upwardly arched from the bowl of the stethoscope head. The acoustical stiffness of the diaphragm is varied by varying the pressure with which it is applied to the body. In this manner, the frequency response to the stethoscope is said to be widened. It is believed, however, that, as with the stethoscope head described in U.S. Pat. No. 3,109,508, the minimum acoustical stiffness of the diaphragm of the stethoscope head is not low enough to optimize sensitivity to low frequency sounds since the diaphragm is tightly clamped around its periphery. The prior stethoscope head constructions and prior methods for using the stethoscope heads emphasize the need for tension in the diaphragm to enhance response to sounds. The prior art also emphasizes the need to tightly clamp the diaphragm at the periphery to prevent sound leaks. Examples of other attempts to broaden the frequency response range of the diaphragm head are found in U.S. Pat. Nos. 3,179,204 and 3,307,650. However, in each case, the diaphragm is tightly affixed at the periphery.

In the past, the bell side of a traditional stethoscope head has been more versatile than the diaphragm side. By decreasing the pressure with which the bell is applied to the skin, sounds at the lower end of the lower frequency have been accentuated. The lower limit, for this decreased pressure, is that point at which the periphery of the bell no longer completely stops sound leaks. When sound leaks in or out, the efficacy of the bell is compromised. Sound energy is either lost from within the bell, resulting in reduced efficacy, or interference leaks in, masking the sounds to be monitored. Increasing the pressure with which the bell is applied to the skin begins to approximate the results attainable from a diaphragm. The skin is stretched over the rim of the bell, causing the skin to respond much as a diaphragm. Sounds in the high frequency range are thereby accentuated. The upper limit for this increased pressure is the point at which the skin actually enters the volume of the bell and appreciably blocks the central sound aperture.

The diaphragm, on the other hand, has not been as traditionally versatile. Increasing the pressure with which the diaphragm is applied to a patient's skin has a lesser effect on the already stiff system. Conversely reduction of application pressure cannot relax the diaphragm below its natural state of tension as it has been traditionally secured in the past.

The advantages of a diaphragm, over a bell, in use in monitoring internal body sounds are many. First, it need not be applied to the skin with as much force as the bell since leaks are prevented by the seal between the diaphragm and the periphery of the chest piece, and sound is transmitted through the sealed diaphragm rather than relying on the seal formed between the entire periphery and the skin, as in the case of the bell. Similiarly, the volume of the diaphragm side of the stethoscope need not be nearly as great as that of the bell. That is primarily because there is no risk of skin entering the volume and thereby blocking the sound aperture. This has, in the past, resulted in slimmer diaphragm head constructions than bell constructions. This is particularly important when the stethoscope is used under clothing. Also, since the diaphragm need not be applied with great force to the skin to create a seal, but instead only lightly contact the skin, it is particularly useful in accident cases where it may be quickly and efficiently employed without removing the garments of the patient. It may actually be used over clothing when removal is not practical.

The stethoscope head of the present invention takes advantage of the many desirable features of the diaphragm head and renders the diaphragm more versatile by broadening the frequency response range by improved means of attaching the diaphragm to the chest piece.

SUMMARY OF THE INVENTION

According to the invention, there is provided a stethoscope head comprising a diaphragm that is loosely affixed at its periphery to the head, rather than tightly affixed as in the stethoscope heads of the prior art. This provides a "floating" diaphragm having a greatly increased frequency response range. The stethoscope head comprises a body having a bore therein, a diaphragm head connected to the body including a sound receiving portion and having an aperture therein communicating with the bore to conduct sound from the sound receiving portion into the bore, a hollow stem snugly fitted into the bore and having at least one opening capable of alignment with the bore, a diaphragm including upper and lower surfaces mounted across the sound receiving portion, and retaining means for mounting the diaphragm. The improvement according to the present invention is characterized in that the sound receiving portion includes a substantially planar peripheral surface capable of mating with the peripheral portion of the upper surface of the diaphragm to prevent the passage of sound energy there between and further characterized in that the retaining means includes means for loosely mounting the diaphragm at its periphery whereby movement of the diaphragm in a plane perpendicular to the plane of the upper surface of the diaphragm is permitted and whereby mating of the peripheral portion of the upper surface of the diaphragm and the substantially planar peripheral surface of the sound receiving portion is permitted to prevent the passage of sound energy there between.

The new, loosely affixed, diaphragm construction allows the diaphragm to respond much as a bell responds in the low frequency range and as a traditional diaphragm responds in the high frequency range. It eliminates the need to employ multiple heads in the detection of sounds normally monitored within the human body. The physician may rapidly alternate between the monitoring of low frequency and high frequency sounds without removing the diaphragm from the skin and without losing the impression from the previously-heard sound before the next sound is monitored. The elimination of multiple heads allows for slimmer constructions and increased versatility in use. It may be easier used under clothing. It is also more responsive over clothing, particularly when monitoring low frequency sounds.

Other objects and advantages of the invention will become apparent from the following drawings wherein like numerals refer to like parts, the accompanying description and the appended claims.

DESCRIPTION OF THE PREFERRED EMBODIMENT

Figure 1:
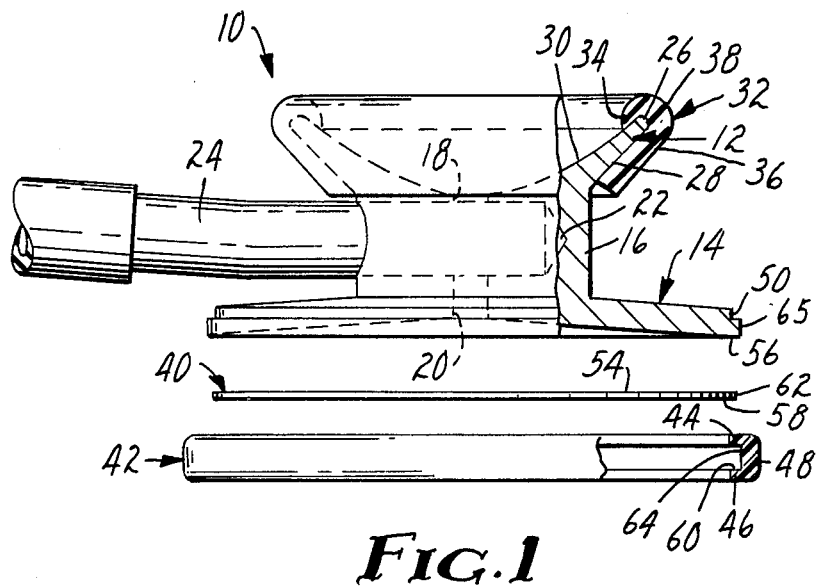
FIG. 1 an exploded, side elevational view, with parts broken away and parts in section, of a stethoscope head with a loosely-affixed diaphragm.

Referring to the drawings wherein like reference characters designate like parts throughout the several views, a stethoscope head 10 is shown with a conventional bell-shaped open bell 12 in back-to-back relation with a diaphragm head 14 separated by an intermediate body portion 16. At the apex of bell 12 and diaphragm head 14 are aligned apertures 18 and 20 respectively. Apertures 18 and 20 communicate with bore 22 through body 16. Apertures 18 and 20 are aligned substantially perpendicular to the longitudinal axis of bore 22.

Body 16 is fitted with a conventional tubular stem 24. Stem 24, in turn, is conventionally adapted to rotate within and relative to body portion 16 and has conventional aligning means to align at least one opening (not shown) in stem 24 with either aperture 18 or 20 to provide a sound passageway from the selected and properly aligned bell 12 or diaphragm head 14 to stem 24. Stem 24 is adapted to be connected to a conventional binaural head set (not shown). A specific stethoscope head construction may vary greatly in accordance with known practice and may in some cases comprise a single diaphragm head 14 rather than a dual-head construction such as that illustrated in FIG. 1.

Bell 12 has a continuous peripheral rim 26. Rim 26 lies in a plane spaced outwardly from and at all places equidistant from central aperture 18. This rim is continuous with an outer annular wall 28 and an inner annular wall 30.

An annular cover 32 covers rim 26 of bell 12. Cover 32 is preferably formed of a flexible and resilient material. It may be formed of a neoprene or other synthetic rubber material which may be stretched or distorted to be snapped over rim 26. Cover 32 is formed with opposed and spaced apart annular side walls 34 and 36. Outside wall 36 is longer than inside wall 34. Side walls 34 and 36 are interconnected by an annular web 38 and are relatively thick to provide cushioning cover 32 over rim 26. Web 38 is integral with side walls 34 and 36 and forms the top of cover 32. Side walls 34 and 36 engage the inner side wall 30 and the outer side wall 28 respectively of bell 12 adjacent rim 26 to hold cover 34 in place.

Turning now to the diaphragm side of stethoscope head 10, diaphragm head 14 is shown in FIG. 1 to include a diaphragm 40 and retaining ring 42. Diaphragm 40 is substantially planar and circular in configuration as well known in the art. It may be comprised, for example, of fiberglass and epoxy resin, various plastics, or thin metal sheets. Retaining ring 42 may, similarly, be comprised of a plastic or suitable metal material. Retaining ring 42 has an upper annular ridge 44 and a lower annular ridge 46. Ridges 44 and 46 are interconnected by annular body 48. Body 48 may be integral with ridges 44 and 46.

Figure 2:
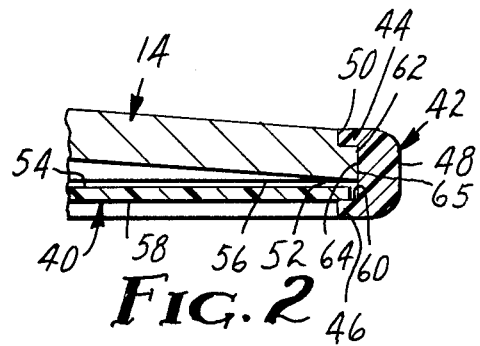
FIG. 2 is an enlarged partial sectional view of the diaphragm head and retaining ring portion of the stethoscope head of FIG. 1.
Figure 3:
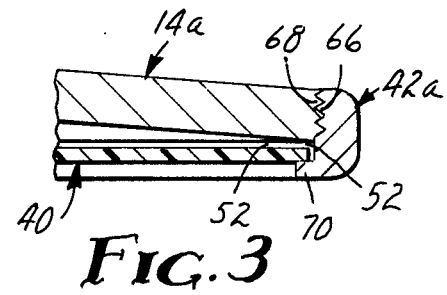
FIG. 3 is an enlarged partial sectional view of an alternative diaphragm head and retaining ring portion for the stethoscope head of FIG. 1.

The assembly of diaphragm 40 and retaining ring 42 with diaphragm head 14 is shown in FIG. 2. Upper annular ridge 44 of retaining ring 42 fits snugly within annular notch 50 of diaphragm head 14. Annular notch 50, as also shown in FIG. 1, is continuous and extends around the periphery of diaphragm head 14. An alternative embodiment is shown in FIG. 3 and is described below.

Referring again to FIG. 2, diaphragm 40 is loosely supported by annular ridge 46 of retaining ring 42. Space 52 is provided between the upper, peripheral surface 54 of diaphragm 40 and the lower, peripheral mating surface 56 of diaphragm head 14. Surface 56 is substantially planar and circular in shape and contacts surface 54 of diaphragm 40 when diaphragm head 14 is pressed against the patient to produce a seal prohibiting the passage of sound energy therebetween. When not pressed against the patient, the lower peripheral surface 58 of diaphragm 40 rests on the upper surface 60 of ridge 46 of retaining ring 42. The diameter of diaphragm 40 is smaller than the inside diameter of body 48 to allow diaphragm 40 to move from surface 60 of ridge 46 to surface 54 of diaphragm head 14 when diaphragm head 14 is pressed against the patient. This is accomplished by diaphragm 40 moving within inside cylindrical side wall 64 of body 48.

Diaphragm head 14 is assembled by first snapping diaphragm 40 between ridge 44 and ridge 46 and resting the surface 58 of diaphragm 40 on surface 60 of ridge 46. Next, ridge 44 is snapped over exterior cylindrical side wall 65 of diaphragm head 14 and snugly fitted within mating notch 50. Once assembled, inside cylindrical side wall 64 of body 48 is juxtaposed and preferably pressed against exterior cylindrical side wall 65 of head 14 by the dimensioning of diaphragm head 14 and body 48, i.e., the outside diameter of diaphragm head 14 is slightly larger than the inside diameter of body 48.

Space 52 must be of sufficient vertical height to allow diaphragm 40 to move freely up and down between surface 60 of ridge 46 and surface 54 of head 14. But at the same time, it must not be so large as to allow diaphragm 40 to fall out of ridge 46. It is generally preferable to have space 52 somewhat smaller than the width of diaphragm 40. This allows relatively free movement of diaphragm 40 while simultaneously preventing diaphragm 40 from falling out of ridge 46. In actual use, the dimensions of diaphragm 40 and space 52 are determined by the overall size of stethoscope head 10 and the radial depth of surface 60 of ridge 46. Again, what is important is that diaphragm 40 be loosely held within ring 42 with sufficient retaining means to prevent dislocation.

An alternative manner of loosely affixing diaphragm 40 is shown in FIG. 3. Space 52 is again provided but by an alternative ring 42a. Ring 42a has a threaded portion 66. Diaphragm head 14a is similarly threaded at periphery 68. Diaphragm head 14a is assembled by first placing diaphragm 40 on ridge 70 of ring 42a much as in the embodiment shown in FIG. 2. Next, ring 42a is screwed onto the diaphragm head 14a leaving space 52 as before. The manner in which diaphragm 40 moves beween ridge 70 and diaphragm head 14a, is, preferably, identical to the manner in which diaphragm 40 moves in FIG. 2. Similarly, the seal formed between diaphragm 40 and diaphragm head 14a at their respective peripheries is identical.

Stethoscope head 10 is used by contacting bell 12 or diaphragm head 14 or 14a with the patient's skin in a manner well known in the art. When diaphragm head 14 is used, upper surface 54 of diaphragm 40 is brought into contact with lower surface 56 of diaphragm head 14 by the pressure provided by the patient's skin. With surfaces 54 and 56 in contact, the sound emanating from beneath the patient's skin is transmitted through the diaphragm 40 into aperture 20. Just the slight pressure and resulting contact between surfaces 54 and 56 is sufficient to prevent loss of sound energy around the periphery. Despite the prior art teachings to the contrary, this peripheral contact need not be clamped tight. There need be only sufficient contact to prevent the passage of sound energy.

Loosely affixing diaphragm 40 at its periphery as shown in FIG. 2 or 3 has certain advantages as alluded to earlier. In summary, this manner of construction allows diaphragm head 14 or 14a to operate in the low frequency range in a manner similar to that previously attainable with a bell without the attendant disadvantages encountered with a bell. This is made possible by tightly controlling the manufacturing tolerances of diaphragm head 14 or 14a to produce a substantially planer lower surface 56. By fully and completely contacting surface 56 with surface 54 of diaphragm 40, sound leakage or introduction between surfaces 56 and 54 are effectively eliminated without the disadvantages associated with tightly clamping the two together as taught by the prior art.

From the foregoing, it will be apparent that all of the objectives of this invention have been achieved by the stethoscope head and loosely affixed diaphragm shown and described. It will also be apparent that various modifications and changes may be made by those skilled in the art without departing from the spirit of the invention as expressed in the accompanying claims. Therefore, all matter shown and described is to be interpretated as illustrative and not in a limiting sense.

What is claimed is:

1. A stethoscope head comprising:
   a. a body having a bore therein;
   b. a diaphragm head connected to the body and having an aperture therein communicating with the bore in the body to conduct sound from the diaphragm head into the bore;
   c. a continuous and peripheral rim connected to the head;
   d. a diaphragm comprising: (1) a first surface adapted to selectively engage the rim to prevent the passage of sound energy there between, (2) a second surface spaced from the first surface and (3) at least a single edge connecting the first surface to the second surface; and
   e. means for loosely affixing the diaphragm to the head whereby the first surface of the diaphragm and the rim are held in close proximity.

2. The stethoscope head recited in claim 1 wherein the affixing means comprises:
   a. means for peripherally supporting the diaphragm; and
   b. means for attaching the supporting means to the head.

3. The stethoscope head recited in claim 2 wherein the supporting means comprises:
   a. a ridge juxtaposed the second surface of the diaphragm opposite the peripheral rim; and
   b. a vertical support juxtaposed the edge of the diaphragm and connected to the ridge.

4. The stethoscope head recited in claim 3 wherein the attaching means comprises:
   a. a second ridge connected to the vertical support; and b. a portion of the head having a notch therein adapted to selectively engage and retain the second ridge.

5. The stethoscope head recited in claim 3 wherein the attaching means comprises:
   a. a portion of the vertical support having threads therein; and
   b. a portion of the head having threads therein adapted to selectively engage the threaded portion of the vertical support.

6. A stethoscope head comprising:
   a. a body having a bore therein;
   b. a diaphragm head connected to the body and having an aperture therein communicating with the bore in the body to conduct sound from the diaphragm head into the bore;
   c. a continuous and peripheral rim connected to the head;
   d. a planar diaphragm having a first surface adapted to contact the rim to prevent the passage of sound energy there between; and
   e. means for loosely affixing the diaphragm to the head whereby (1) the first surface of the diaphragm and the rim are held in close proximity and (2) the first surface and the rim are capable of forming an acoustic seal there between.

7. The stethoscope head recited in claim 6 wherein the affixing means comprises:
   a. means for peripherally supporting the diaphragm; and
   b. means for attaching the supporting means to the head.

8. The stethoscope head recited in claim 7 wherein the supporting means comprises:
   a. a ridge juxtaposed a second surface of the planar diaphragm opposite the peripheral rim; and
   b. a vertical support juxtaposed an edge of the diaphragm and connected to the ridge.

9. The stethoscope head recited in claim 8 wherein the attaching means comprises:
   a. a second ridge connected to the vertical support; and
   b. a portion of the head having a notch therein adapted to selectively engage and retain the second ridge.

10. The stethoscope head recited in claim 8 wherein the attaching means comprises:
    a. a portion of the vertical support having threads therein; and
    b. a portion of the head having threads therein adapted to selectively engage the threaded portion of the vertical support.

11. In a stethoscope head comprising a body having a bore therein, a diaphragm head connected to the body, the diaphragm head comprising a sound receiving portion and having an aperture therein communicating with the bore to conduct sound from the sound receiving portion into the bore; a hollow stem snugly fitted into the bore and having at least one opening capable of alignment with the bore; a diaphragm comprising upper and lower surfaces mounted across the sound receiving portion; and retaining means for mounting the diaphragm; the improvement wherein:
    a. the sound receiving portion comprises a substantially planar peripheral surface capable of mating with a peripheral portion of the upper surface of the diaphragm to prevent the passage of sound energy there between; and
    b. the retaining means comprises means for loosely and peripherally mounting the diaphragm whereby:
       (1) movement of the diaphragm in a plane perpendicular to the plane of the upper surface of the diaphragm is permitted; and
       (2) mating of the peripheral portion of the upper surface of the diaphragm and the substantially planar peripheral surface of the sound receiving portion is permitted whereby the passage of sound energy there between is prevented when the diaphragm is pressed against a surface.

* * * * *

REEXAMINATION CERTIFICATE (2293rd)

United States Patent [19]

Packard

[11] B1 4,475,619

[45] Certificate Issued  May 10, 1994

[54] STETHOSCOPE WITH FLOATING DIAPHRAGM

[75] Inventor: Thomas J. Packard, St. Paul, Minn.

[73] Assignee: Minnesota Mining and Manufacturing Company, St. Paul, Minn.

Reexamination Request:
No. 90/002,497, Oct. 31, 1991

Reexamination Certificate for:
Patent No.: 4,475,619
Issued: Oct. 9, 1984
Appl. No.: 478,222
Filed: Mar. 24, 1983

[51] Int. Cl.⁵ .................. H04R 25/00; A61B 7/02
[52] U.S. Cl. .......................................... 181/137
[58] Field of Search ................ 181/131, 132, 137

[56] References Cited

U.S. PATENT DOCUMENTS

| 1,824,590 | 9/1931 | Bernard . | |
|---|---|---|---|
| 1,876,858 | 9/1932 | Chireix . | |
| 2,651,380 | 9/1953 | Brandenburg . | |
| 2,836,255 | 5/1958 | Reichardt . | |
| 3,223,195 | 12/1965 | Allen . | |
| 3,470,975 | 10/1969 | Haiken | 181/132 |
| 3,684,052 | 8/1972 | Sotome . | |
| 4,387,788 | 6/1983 | Slavin et al. . | |

FOREIGN PATENT DOCUMENTS

543272  12/1973  Switzerland ............... A61B 7/02

*Primary Examiner*—Michael L. Gellner

[57] ABSTRACT

A stethoscope including a diaphragm head with a loosely affixed diaphragm exhibiting an increased frequency response range. The diaphragm is peripherally supported adjacent the rim of the diaphragm head. The diaphragm is contacted with the head by the pressure applied by the underlying skin or clothing of the patient to eliminate sound leakage therebetween.

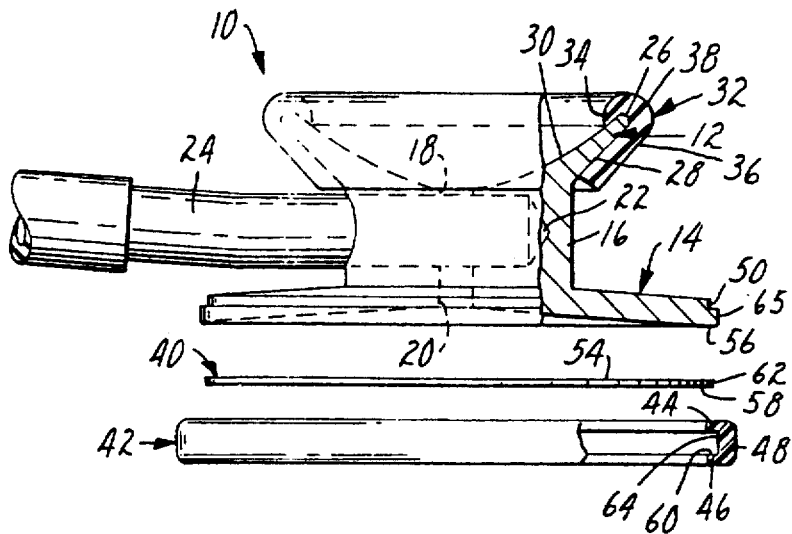

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-11 is confirmed.

* * * * *